(12) United States Patent
Prasitchoke et al.

(10) Patent No.: US 9,012,698 B2
(45) Date of Patent: Apr. 21, 2015

(54) METHOD OF EXTRACTING LUTEIN/XANTHOPHYLLS FROM NATURAL MATERIALS AND HIGHLY PURIFIED LUTEIN/XANTHOPHYLLS OBTAINED FROM THE METHOD THEREOF

(75) Inventors: Phatthanon Prasitchoke, Bangkok (TH); Chaya Chandavasu, Bangkok (TH); Artiwan Shotipruk, Bangkok (TH); Panatpong Boonnoun, Bangkok (TH)

(73) Assignees: PTT Global Chemical Public Company Limited, Bangkok (TH); Chulalongkorn University, Bangkok (TH)

( * ) Notice: Subject to any disclaimer, the term of this patent is extended or adjusted under 35 U.S.C. 154(b) by 0 days.

(21) Appl. No.: 14/241,435

(22) PCT Filed: Aug. 24, 2012

(86) PCT No.: PCT/TH2012/000037
§ 371 (c)(1),
(2), (4) Date: Feb. 26, 2014

(87) PCT Pub. No.: WO2013/032412
PCT Pub. Date: Mar. 7, 2013

(65) Prior Publication Data
US 2014/0200374 A1    Jul. 17, 2014

(30) Foreign Application Priority Data
Aug. 26, 2011 (TH) .................................. 1101001774

(51) Int. Cl.
*C07C 403/24* (2006.01)
*C09B 61/00* (2006.01)

(52) U.S. Cl.
CPC ............ *C07C 403/24* (2013.01); *C09B 61/00* (2013.01)

(58) Field of Classification Search
None
See application file for complete search history.

(56) References Cited

U.S. PATENT DOCUMENTS

| | | |
|---|---|---|
| 4,466,923 A | 8/1984 | Friedrich |
| 5,120,558 A | 6/1992 | Nguyen et al. |
| 5,780,693 A | 7/1998 | Bernhard et al. |
| 5,932,101 A | 8/1999 | Kanel et al. |
| 6,262,284 B1 | 7/2001 | Khachik |
| 6,350,890 B1 | 2/2002 | Kiy et al. |
| 6,689,400 B2 | 2/2004 | Majeed |
| 6,737,552 B1 | 5/2004 | Crombie |
| 7,214,379 B2 | 5/2007 | Sadano et al. |
| 7,351,424 B2 | 4/2008 | Ornelas-Cravioto et al. |
| 2004/0267033 A1 | 12/2004 | Rao et al. |

FOREIGN PATENT DOCUMENTS

| | | |
|---|---|---|
| CN | 1364831 | 8/2002 |
| WO | 2004018417 | 3/2004 |
| WO | 2005068409 | 7/2005 |

OTHER PUBLICATIONS

Database CAPLUS in STN, Acc. No. 2008:446495, Nie et al., Riyong Huaxuepin Kexue (2008), 31(1), pp. 15-18 (abstract).*
International Application No. PCT/TH2012/000037, International Search Report and Written Opinion mailed Dec. 5, 2012.

* cited by examiner

*Primary Examiner* — Brian J Davis
(74) *Attorney, Agent, or Firm* — Sheppard, Mullin, Richter & Hampton LLP

(57) ABSTRACT

The present invention provides the new method for extracting lutein from natural materials wherein the said method comprises of modification of natural lutein ester in the natural materials to free lutein and/or low molecular weight lutein ester, extraction of the said natural materials with supercritical fluid at the optimal conditions. The said method yields high amount of crude lutein with high purity due to the mild condition used for extraction. Therefore, no degradation of the desired product is occurred. The crude lutein can be further purified with chromatography in order to obtain the highly purified lutein. The method according to this invention can be applied to the extraction of xanthophylls or others beside lutein.

12 Claims, 2 Drawing Sheets

US 9,012,698 B2

METHOD OF EXTRACTING LUTEIN/XANTHOPHYLLS FROM NATURAL MATERIALS AND HIGHLY PURIFIED LUTEIN/XANTHOPHYLLS OBTAINED FROM THE METHOD THEREOF

CROSS-REFERENCE TO RELATED APPLICATIONS

This application is a national stage application pursuant to 35 U.S.C. §371 of International Application No. PCT/TH2012/000037, filed Aug. 24, 2012, which claims priority to TH Patent Application No. 1101001774, filed Aug. 26, 2011, the disclosures of which are hereby incorporated by reference herein.

FIELD OF THE INVENTION

Organic chemistry related to the extraction of lutein/xanthophylls, especially the extraction of lutein from marigold flowers with supercritical fluid, and highly purified lutein/xanthophylls obtained from the method thereof.

Marigold (*Tagetes erecta*) is an annual flowering plant having tube-like petals in a wide range of colors. In Thailand, marigolds are cultivated mainly in Suphanburi, Kanchanaburi, Lampoon and Chiang Mai provinces. Due to the high content of carotenoids, marigolds are commonly used in animal feeds for the animals' health benefits. Moreover, the bright yellow and red colors of carotenoids in marigold are also used as natural colorants in feeds (e.g., in chicken feed, which yields egg yolk with a bright red color).

The major carotenoids in marigold are xanthophylls (up to 1%), especially lutein.

Lutein is a xanthophyll which exhibits antioxidative properties and is included in the composition of retina in the eye. It has been reported that lutein can be used effectively for the treatment of diseases related to vision and also used for maintaining functions in the human body. Therefore, the method of extracting lutein from natural materials is of interest.

One of the attempts is to extract lutein from marigold by an organic solvent, especially a non-polar solvent such as hexane. The material contained in the organic solvent is called miscellar. To obtain the lutein product, the remaining solvent must be evaporated. The crude extract obtained after solvent evaporation is called oleoresin. The oleoresin contains 10% (w/w) xanthophylls, of which lutein is the major product.

One of the problems is the strict requirement of absolute removal of the extraction solvent. The remaining solvent must not exceed the international standard. This is due to the fact that remaining solvent may cause serious health problems to consumers.

There has been an attempt to extract lutein by using an alternative solvent (i.e., a supercritical fluid, especially supercritical carbon dioxide) which is safer to use for consumer products. Moreover, supercritical carbon dioxide possesses high diffusivity and low viscosity when compared to liquid solvents. Supercritical carbon dioxide is, therefore, suitable for extraction due to its mass transfer property. Moreover, it can be used for the extraction at low temperature (critical temperature is 30° C.), which prevents the decomposition or degradation of the extracted materials. It can also be removed easily by pressure reduction or temperature reduction.

U.S. Patent Application Pub. No. 2004/0267033 describes the extraction of lutein from marigold by supercritical carbon dioxide at 70° C. and 475 bar, gaining 85-90% yield. The problem with this invention is that a high temperature must be used in order to obtain xanthophylls with a high purity, which is required for use in nutraceuticals or drugs. The problem associated with increasing temperature during the extraction is the degradation or decomposition of xanthophylls, whereas the increase in pressure also consumes more energy and poses more risks. Therefore, the supercritical fluid cannot be practically used for the industrial extraction of xanthophylls, especially highly purified lutein. The method according to the above invention still has problems with the extreme conditions even though it can solve the safety problem of liquid solvents.

Other related documents include U.S. Pat. Nos. 4,466,923; 5,120,558; 5,932,101; 6,737,552; 6,350,890; 7,214,379; 5,780,693; 6,262,284; 7,351,424; and 6,689,400.

The applicant studied the problems in the prior art and the natural properties of lutein and other xanthophylls in nature. It was found that lutein and other xanthophylls in nature are mostly in the form of a diester with a fatty acid (e.g., lutein dipalmitate, lutein dimyristate, zeaxanthine dipalmitate and zeaxanthine dimyristate). These diesters have high molecular weights (e.g., lutein dipalmitate has a molecular weight of 1045 Dalton whereas free lutein has a molecular weight of only 569 Dalton). Consequently, the extraction of natural lutein/xanthophylls from these complex molecules with supercritical fluid would require high temperature and/or high pressure to obtain a yield of lutein/xanthophylls similar to the solvent extraction method.

The applicant performed the extraction of lutein from natural materials directly with supercritical fluid at a reduced temperature of 60° C. and varied the condition of pressure at 300, 350 and 400 bar, respectively, for 4 hours as shown in FIG. 1.

FIG. 1 shows the yield of crude lutein obtained from extraction. Although the yield of crude lutein is increased by increasing the pressure, the maximum yield is only 74.40% at 400 bar.

Moreover, the applicant applied the crude lutein to chromatography purification and found that the free lutein was mixed with a very high amount of lutein ester, as shown in FIG. 2.

Until now, there has been no report of extraction of crude natural lutein with supercritical fluid at low temperature and pressure with a product yield higher than 90%.

Therefore, the applicant aimed to modify lutein ester/xanthophylls esters to free lutein/xanthophylls and/or low molecular weight lutein ester/xanthophyll esters before extraction with supercritical fluids. Natural materials containing lutein/xanthophylls include marigold, kale, spinach, and microbial cells (e.g., bacteria, yeasts, fungi, microalgae and *algae*). This invention allows the extraction of crude lutein from natural materials with supercritical fluids at low temperature and pressure but still provides a high yield.

SUMMARY OF THE INVENTION

The present invention provides a new method for extracting lutein from natural materials which yields higher crude lutein and/or higher purified lutein than previously existing methods.

Another objective of this invention is to provide an extraction method which is applicable to xanthophylls, which are in the same group of compounds as lutein.

Another objective of this invention is to provide highly purified lutein/xanthophylls obtained from the methods according to the present invention.

The method according to this invention includes the modification of natural lutein ester in the natural materials to free lutein and/or low molecular weight lutein ester, and the extraction of the natural materials with supercritical fluid at optimal conditions. The method according to this invention is capable of lutein extraction from natural materials in high amount because the efficiency of extraction is improved. The crude lutein can be further purified with chromatography in order to obtain highly purified lutein.

DETAILED DESCRIPTION

Figure 1:
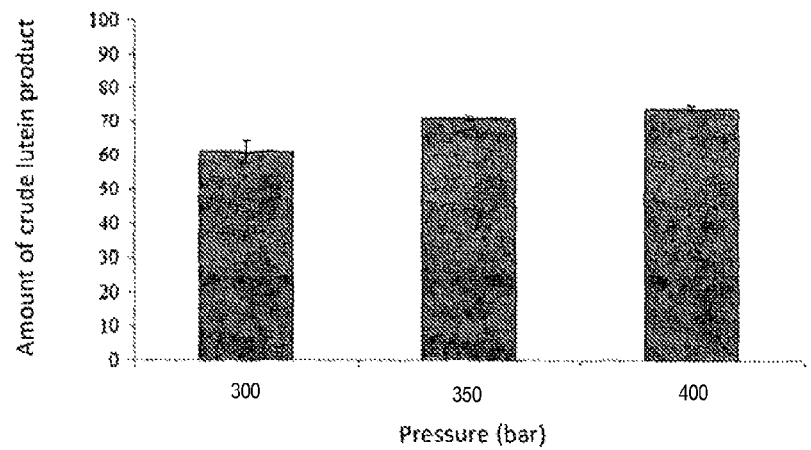
FIG. 1 is a chart displaying the yield of crude lutein which is extracted from natural materials directly by supercritical fluid at 60° C., pressure 300, 350 and 400 bar.

In this invention, "crude lutein" means crude product which contains lutein as the finished product.

When the method according to this invention is applied to xanthophylls other than lutein, "crude lutein" means the crude product of xanthophylls other than lutein. Therefore, the words "lutein" and "xanthophylls" are interchangeable throughout the disclosure.

Details of the extraction method of lutein from natural materials according to this invention are described below.

The method for extracting natural lutein comprises:

(a) Pretreatment of natural materials containing lutein by modification of natural lutein ester in the natural materials to free lutein and/or low molecular weight lutein ester, which facilitates the extraction process.

(b) Extraction comprising contacting the pretreated natural materials in (a) with supercritical fluid, adjusting temperature and/or pressure by selecting the optimal condition between 30-100° C., 200-450 bar for a certain period of time to allow the maximum solubility of free lutein and/or low molecular weight lutein ester in the supercritical fluid.

(c) Separation of solid materials from the fluid after extraction, adjusting temperature and/or pressure to minimize the solubility of extracted materials in the fluid, and collecting of the extracted materials (i.e., the crude lutein).

According to the method, the natural materials can be selected from marigold flower, kale, spinach, algae, and microbial cells including bacteria, yeasts, fungi and microalgae.

According to the method, the natural materials are hydrolyzed with low molecular weight acid, followed by removing of the acid by washing with water and/or drying and/or grinding before subjecting the natural materials to step (a). The acids can be organic acids (e.g., acetic acid) or inorganic acids (e.g., hydrochloric acid).

The modification of lutein ester in step (a) is saponification, which is widely used. For example, the saponification can be done by using KOH and ethanol at the optimal temperature and time depending on the natural materials used. The modification of lutein ester may be achieved by esterification with a low molecular weight acid (e.g., hydrochloric acid) and ethanol, or by transesterification using KOH and methanol.

The supercritical fluid according to this invention can be selected from carbon dioxide, ethanol or a combination thereof. However, carbon dioxide is preferable.

In some cases, depending on the natural materials used as raw material, a co-solvent such as a non-toxic natural oil (e.g., palm oil, soybean oil, olive oil or a combination thereof) can be used together with the supercritical fluid in order to improve the extraction efficiency.

In the extraction with supercritical fluid in step (b), the optimal condition is between 40-70° C., 300-400 bar. This condition yields maximum crude lutein because of the "not too high" temperature and pressure when compared to the existing methods.

Moreover, the method for extraction may further comprise step (d): purification of the crude lutein by chromatography.

This invention also relates to the crude product of lutein obtained from the extraction method previously described and the purified lutein obtained from chromatography.

It is important to note that this invention does not use solvent, which may cause (partial) degradation during the solvent removal. This invention employs the modification of lutein ester in natural materials directly. This has the advantage of no waste of lutein before the extraction with fluid. Meanwhile, the extraction should also provide a smooth and more effective flow due to the reduced molecular weight that results from extracting target compounds.

Below are examples with reference to the drawings; however, these examples are not intended to limit the scope of the invention.

EXAMPLES

Hydrolysis

Fresh petals of marigold were hydrolyzed with a low molecular weight acid (e.g., acetic acid or hydrochloric acid) in order to break down celluloses for 30 minutes. The hydrolyzed petals were washed with water and then dried or sun-dried and ground to form powder.

Modification (Modification of Lutein Ester in Natural Materials to Free Lutein or Lutein Esters with Low Molecular Weight)

One gram of hydrolyzed powder of marigold was added to 2 ml of 95% ethanol at a temperature of 75° C. Then 2 ml of 40% alkaline solution was added and incubated at 75° C. for 4 hours. The solution was cooled to 65° C. and pH was adjusted to 7 using 25% hydrochloric acid in order to terminate the saponification. The solution was then dried.

Extraction with Supercritical Carbon Dioxide

In this step, a 10 ml supercritical carbon dioxide extractor (model SFX-220, ISCO) was used. Saponified marigold powder (1 g) was added to the extractor before allowing the supercritical carbon dioxide to contact the powder. Temperature and/or pressure was selected to optimal condition between 40-120° C., 200-500 bar for 4 hours or other duration in order to maximize the solubility of free lutein and/or lutein ester with low molecular weight in the supercritical carbon dioxide. The optimal condition should be between 35-70° C. and 300-400 bar. The system allows the recycling of carbon dioxide or optionally the release of carbon dioxide to the atmosphere.

The applicant performed experiments by selecting the following conditions:

1) Temperature 40° C., pressure 150, 200, 250, 300, 350 and 375 bar;
2) Temperature 60° C., pressure 150, 200, 250, 300 and 325 bar;

3) Temperature 80° C., pressure 150, 200, 250 and 290 bar;
4) Temperature 100° C., pressure 150, 200, 250 and 275 bar; and
5) Temperature 120° C., pressure 150, 200 and 255 bar.

Figure 3:
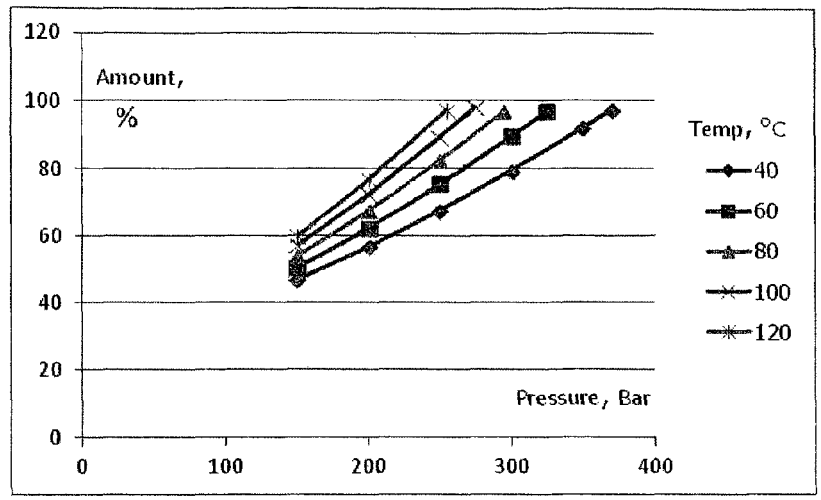
FIG. 3 is a chart displaying the yield of crude lutein extracted (from natural materials after modification of lutein ester in marigold) by supercritical fluid at temperature and pressures according to this invention.

The yields of crude lutein products obtained from the above experiments are shown in the graph in FIG. 3. From FIG. 3 it can be seen that at a temperature of 40° C. and pressure 375 bar, the yield of crude lutein is 98.5%, and at a temperature of 60° C. and pressure 325 bar, the yield of crude lutein is also 98.5%.

In conclusion, if low temperature is used, a higher pressure is required in order to maximize the yield of lutein. In contrast, if a higher temperature is used, a lower pressure can then be applied. However, too high of a temperature and a lack of an oxidation protecting agent will cause the degradation or decomposition of lutein at an unacceptable level.

When comparing the results of the method according to this invention in FIG. 3 and the results of the prior art method in FIG. 1, it is shown that at a temperature of 60° C., the method according to this invention only requires pressure at 375 bar to yield crude lutein up to 98.5%, whereas the pressure in the prior art method must be at 400 bar and the yield of crude lutein is only 74.40%. It can be concluded that the method according to this invention is more efficient.

As indicated by FIG. 3, the extraction using the method according to this invention can be done at a temperature as low as 30° C.

Separation of Debris and Collecting of Crude Lutein

After extraction is completed, the debris is separated. The remaining solution is adjusted to the temperature and/or pressure which allows the minimum solubility of the extracted material in the carbon dioxide. The carbon dioxide is then evaporated and the crude extract (i.e., the crude lutein) is collected in a glass tube wrapped with aluminum foil and stored in the dark at 4° C.

Purification

Purification of free xanthophylls obtained from free xanthophyll esters and fatty acids is performed in normal phase chromatography using a 35 mm×240 mm silica column (100 g silica). A mobile phase comprising 70:30 hexane:ethyl acetate is pumped into the column at a flow rate of 5-10 ml/min by a peristaltic pump. The samples are collected at 10 minute intervals. At a flow rate of 10 ml/min, xanthophylls with a purity of 99.5% are obtained with a yield of 46%, as shown in FIG. 4.

Figure 2:
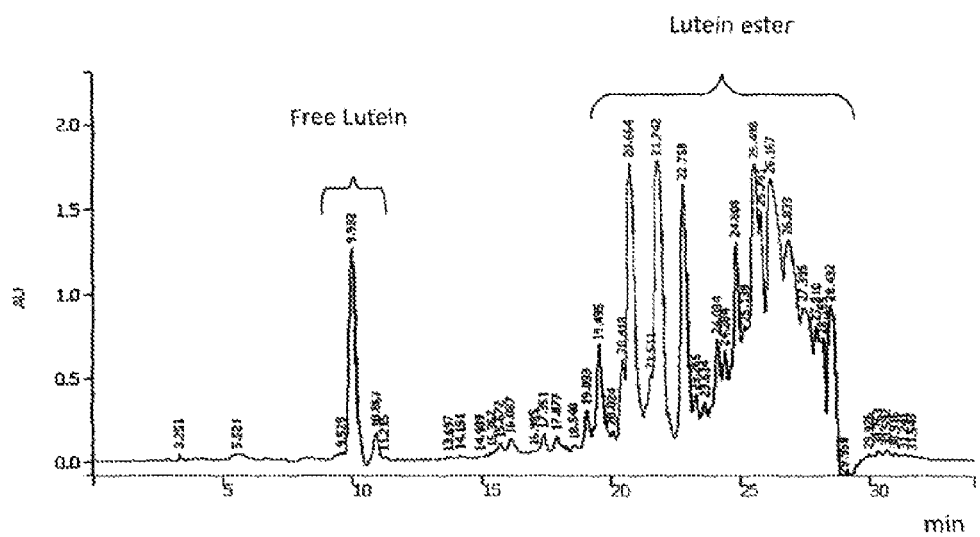
FIG. 2 is a chromatogram of the crude lutein obtained in FIG. 1 showing a small amount of free lutein and a high amount of lutein ester.
Figure 4:
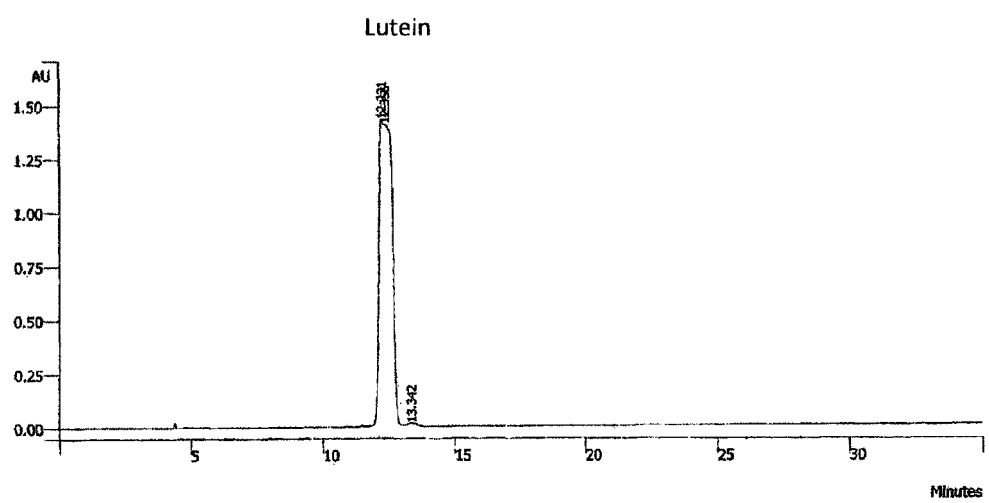
FIG. 4 is a chromatogram of the crude lutein obtained in FIG. 3 showing a high amount of free lutein, which is also highly purified.

FIG. 4 shows the chromatogram of crude lutein as present in FIG. 3, which indicates that the amount of lutein in the crude lutein product is higher than the amount obtained from the prior art method. FIG. 4 also shows that the crude lutein product is almost pure lutein (100%), whereas the crude lutein product obtained by the prior art method contains a high amount of lutein ester, as shown in the chromatogram in FIG. 2.

Although marigold was used in this example as a sample of natural materials, the method according to this invention can also be applied to other natural materials containing lutein (e.g., kale, spinach, and microbial cells including bacteria, yeasts, fungi, microalgae and algae).

A person skilled in the art can also modify this invention and such modification is also considered to be within the scope of this invention. A person skilled in the art also understands that the principle of the extraction method according to this invention can be applied to extraction of xanthophylls (with or without lutein) from natural materials containing xanthophylls by adjusting the conditions to be suitable for the natural materials and selected xanthophylls.

BEST MODE

The best mode of practicing the invention is described in the detailed description.

The invention claimed is:

1. A method of extracting lutein from natural materials, the method comprising:
   (a) pretreating natural materials containing natural lutein esters by modifying the natural lutein esters in the natural materials to obtain free lutein;
   (b) extracting the free lutein by contacting the natural materials pretreated in step (a) with a supercritical fluid, and by adjusting temperature to between 30-100° C. and/or pressure to between 200-450 bar for a period of time to provide the free lutein in a solution with the supercritical fluid;
   (c) separating solid materials from the solution; and
   (d) adjusting temperature and/or pressure to reduce solubility of extracted materials in the solution, wherein the extracted materials comprise crude lutein.

2. The method according to claim 1 wherein the natural materials are selected from marigold flower, kale, spinach, algae, microbial cells or a combination thereof.

3. The method according to claim 1 or 2 wherein the natural materials are hydrolyzed with low molecular weight acid, followed by removing of the acid by washing with water and/or drying and/or grinding, before subjecting the natural materials to step (a).

4. The method according to claim 1 or 2 wherein the modifying of the natural lutein ester in step (a) comprises saponification.

5. The method according to claim 1 or 2 wherein the modifying of the natural lutein ester in step (a) comprises transesterification.

6. The method according to claim 1 wherein the supercritical fluid is selected from carbon dioxide, ethanol or a combination thereof.

7. The method according to claim 6 wherein the supercritical fluid is carbon dioxide.

8. The method according to any claim of claim 1, 2, 6, or 7 wherein the method further comprises using co-solvents with the supercritical fluid, wherein the co-solvents are selected from non-toxic natural oils.

9. The method according to any claim of claim 1, 2, 6, or 7 wherein the temperature condition in step (b) is selected to be between 40-70° C., and/or the pressure condition in step (b) is selected to be between 300-400 bar.

10. The method according to claim 1 wherein the method further comprises purification of the crude lutein by chromatography.

11. The method according to claim 2 wherein the microbial cells are selected from bacteria, yeast, fungi, microalgae or a combination thereof.

12. The method according to claim 8 wherein the non-toxic natural oils are selected from palm oil, soybean oil, olive oil or a combination thereof.

* * * * *